(12) United States Patent
Boileau et al.

(10) Patent No.: US 12,714,413 B2
(45) Date of Patent: Aug. 25, 2026

(54) SURGICAL FIXATION DEVICES AND METHODS OF USE THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Pascal Boileau, Nice (FR); Alexander I. Seidl, Zurich (CH); Dirk Wunderle, Zurich (CH); Mason J. Bettenga, Memphis, TN (US); Jeffrey Wyman, Naples, FL (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 560 days.

(21) Appl. No.: 17/778,715

(22) PCT Filed: Nov. 5, 2020

(86) PCT No.: PCT/US2020/059175
§ 371 (c)(1),
(2) Date: May 20, 2022

(87) PCT Pub. No.: WO2021/101724
PCT Pub. Date: May 27, 2021

(65) Prior Publication Data

US 2022/0409197 A1 Dec. 29, 2022

Related U.S. Application Data

(60) Provisional application No. 62/939,105, filed on Nov. 22, 2019.

(51) Int. Cl.
*A61B 17/04* (2006.01)
*A61B 17/56* (2006.01)
(Continued)

(52) U.S. Cl.
CPC ........ *A61B 17/0401* (2013.01); *A61B 17/842* (2013.01); *A61B 2017/0414* (2013.01);
(Continued)

(58) Field of Classification Search
CPC .............. A61B 17/0401; A61B 17/842; A61B 2017/0414; A61B 2017/0417;
(Continued)

(56) References Cited

U.S. PATENT DOCUMENTS 2,143,086 A * 1/1939 Pieister ................. F16B 13/068 411/28
2,453,056 A * 11/1948 Zack ...................... A61B 17/11 285/71

(Continued)

FOREIGN PATENT DOCUMENTS

EP 1645247 A1 * 4/2006 ............ A61F 2/0811
FR 2931058 A1 * 11/2009 ............ A61F 2/0811
WO WO-2017218167 A1 * 12/2017 ......... A61F 2/30749

*Primary Examiner* — Tan-Uyen T Ho
*Assistant Examiner* — Osama Nemer
(74) *Attorney, Agent, or Firm* — ArentFox Schiff LLP; Joseph M. Maraia

(57) ABSTRACT

A suspension fixation device includes a first fastener assembled to an adjustable loop of suture. The second fastener has a slot configured to allow the second fastener to be assembled to the suture loop once the suture loop has been passed through a drill hole. The second fastener further comprises a suture bridge formed through a post of the fastener for housing the suture loop while the slot is configured to prohibit the suture loop from migrating back out of the suture bridge.

14 Claims, 7 Drawing Sheets

(51) Int. Cl.
*A61B 17/84* (2006.01)
*A61B 17/68* (2006.01)

(52) U.S. Cl.
CPC ................. *A61B 2017/0417* (2013.01); *A61B 2017/0438* (2013.01); *A61B 2017/564* (2013.01); *A61B 2017/681* (2013.01)

(58) Field of Classification Search
CPC ...... A61B 2017/0438; A61B 2017/564; A61B 2017/681; A61B 2017/06185
See application file for complete search history.

(56) References Cited

U.S. PATENT DOCUMENTS 4,011,602 A * 3/1977 Rybicki ................ A61F 2/3662 606/76
4,870,957 A * 10/1989 Goble ................... A61F 2/0811 623/13.12
4,997,433 A * 3/1991 Goble ................... A61F 2/0811 606/62
5,129,906 A * 7/1992 Ross ....................... C08L 77/12 606/77
5,258,015 A * 11/1993 Li ........................ A61B 17/685 24/453
5,258,016 A * 11/1993 DiPoto ................... A61B 90/06 606/232
5,720,766 A * 2/1998 Zang .................... A61B 17/888 606/232
6,063,106 A * 5/2000 Gibson .............. A61B 17/0401 606/232
6,117,161 A * 9/2000 Li ...................... A61B 17/0401 606/232
6,126,677 A * 10/2000 Ganaja .................. A01K 91/03 606/232
6,431,500 B1 * 8/2002 Jacobs ...................... F16L 3/13 248/51
D480,942 S * 10/2003 Ishida ............................ D8/356
7,455,683 B2 * 11/2008 Geissler ................ A61F 2/0811 606/232
7,632,293 B2 * 12/2009 Hartmann .......... A61B 17/7031 606/255
8,545,535 B2 * 10/2013 Hirotsuka .......... A61B 17/0401 606/232
8,876,900 B2 * 11/2014 Guederian ......... A61B 17/0401 623/13.17
9,259,217 B2 * 2/2016 Fritzinger .......... A61B 17/0401
9,265,600 B2 * 2/2016 Niese ..................... A61B 17/04
9,451,945 B2 * 9/2016 Hawkins ............ A61B 17/0401
9,788,838 B2 * 10/2017 McClellan ......... A61B 17/0469
10,238,494 B2 * 3/2019 McNiven ................ A61F 2/246
2002/0120274 A1 * 8/2002 Overaker ........... A61B 17/0642 606/908
2002/0120292 A1 * 8/2002 Morgan ............. A61B 17/1796 606/232
2002/0161439 A1 * 10/2002 Strobel ................ A61F 2/0805 623/13.14
2002/0173788 A1 * 11/2002 Bojarski ........... A61B 17/0401 606/60
2002/0188305 A1 * 12/2002 Foerster ................ A61F 2/0811 606/151
2005/0192632 A1 * 9/2005 Geissler ................ A61F 2/0811 606/232
2006/0282119 A1 * 12/2006 Perchik ............. A61B 17/0401 606/232
2007/0016208 A1 * 1/2007 Thornes ................. A61B 17/68 606/331
2007/0073342 A1 * 3/2007 Stone ................. A61B 17/0401 606/232
2007/0112352 A1 * 5/2007 Sorensen ........... A61B 17/0401 606/326
2008/0306511 A1 * 12/2008 Cooper ............. A61B 17/0401 606/232
2010/0082072 A1 * 4/2010 Sybert .................. A61B 17/686 606/86 R
2011/0054609 A1 * 3/2011 Cook .................. A61F 2/30756 623/13.12
2012/0310279 A1 * 12/2012 Sikora ................ A61B 17/0401 606/232
2013/0123841 A1 * 5/2013 Lyon .................. A61B 17/0401 606/232
2013/0172944 A1 * 7/2013 Fritzinger .......... A61B 17/0401 606/232
2014/0114352 A1 * 4/2014 Allen ................ A61B 17/0487 606/232
2014/0155937 A1 * 6/2014 Shinde ............... A61B 17/0401 606/232
2014/0277185 A1 * 9/2014 Boileau .............. A61B 17/8888 606/86 R
2014/0358230 A1 * 12/2014 Niese ................. A61B 17/0401 623/13.14
2015/0018878 A1 * 1/2015 Rizk ..................... A61L 31/127 606/232

* cited by examiner

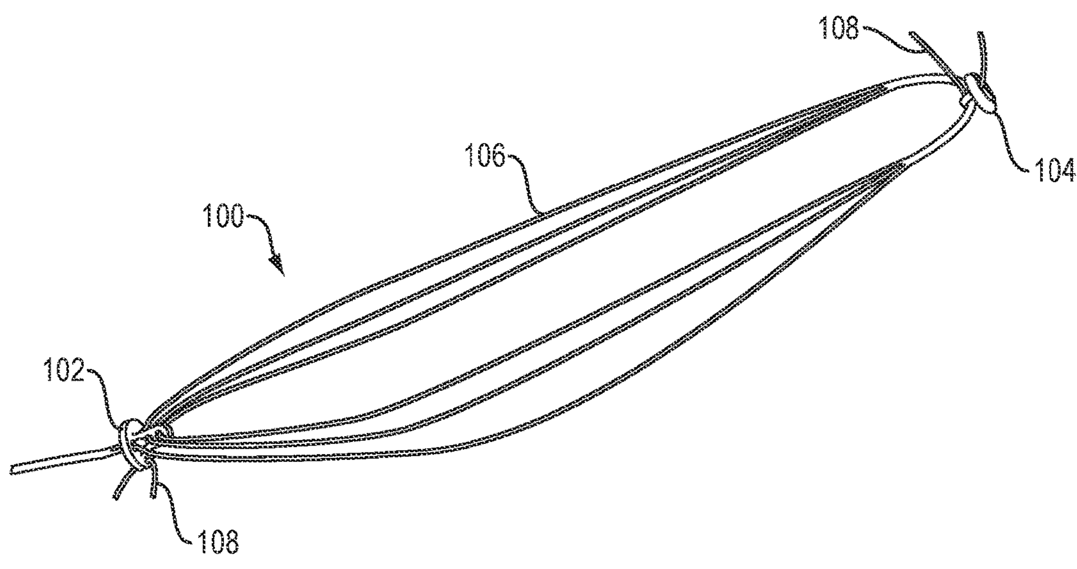
FIG. 1A
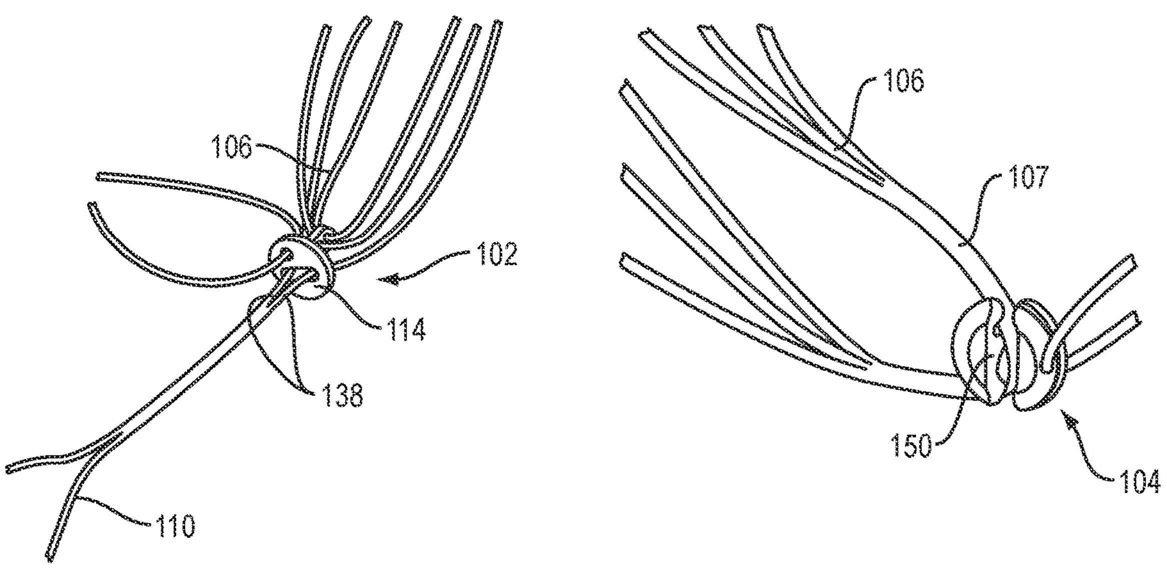
FIG. 1B
FIG. 1C

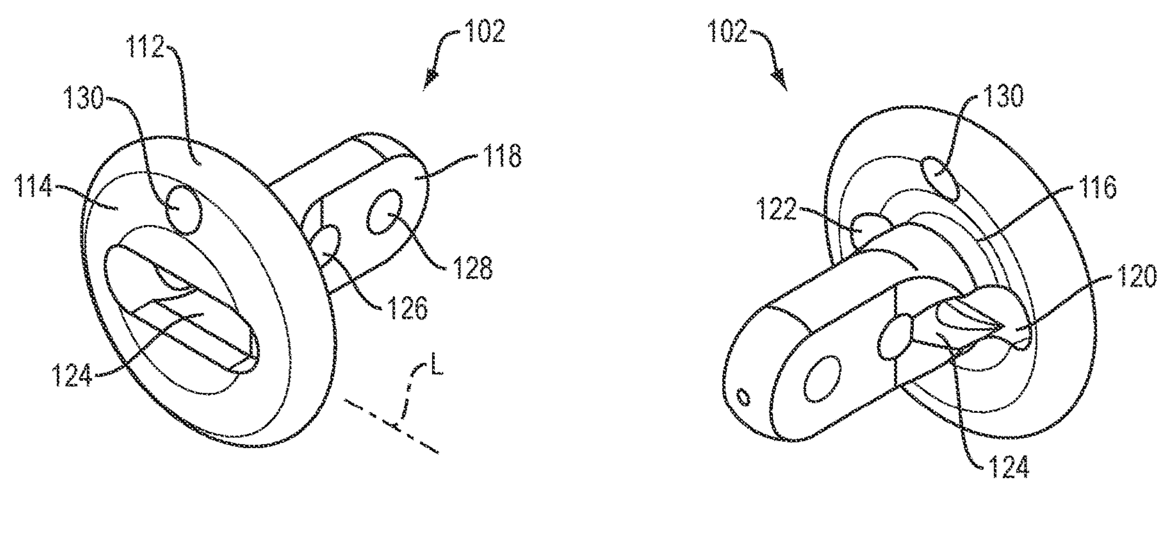
FIG. 2A
FIG. 2B
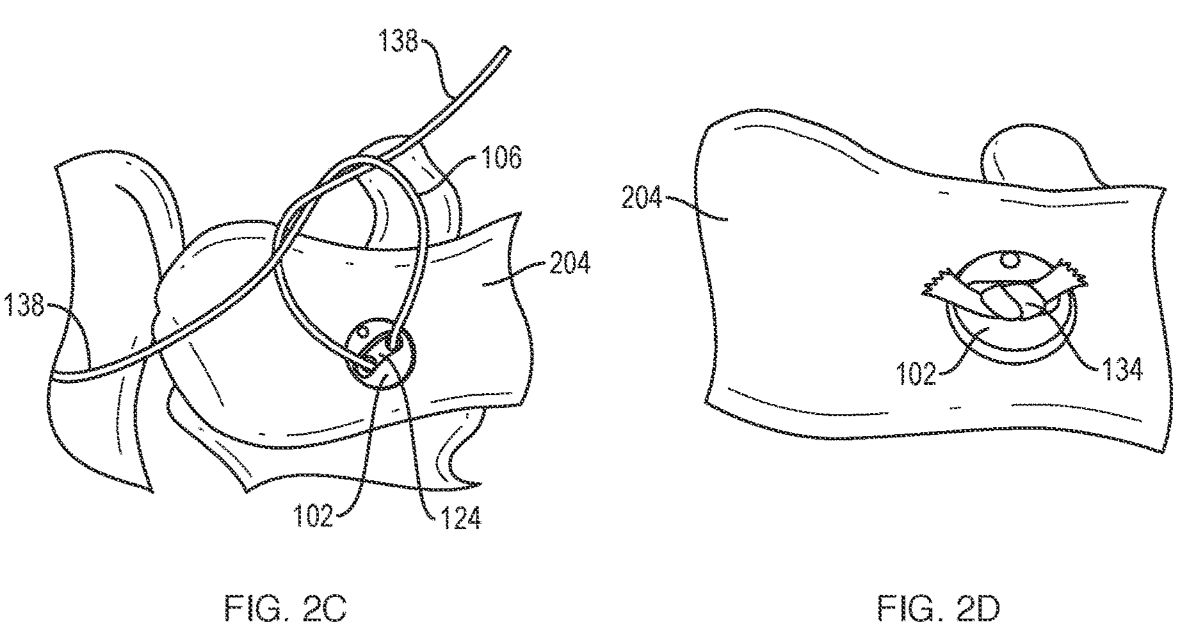
FIG. 2C
FIG. 2D

SURGICAL FIXATION DEVICES AND METHODS OF USE THEREOF

CROSS-REFERENCE TO RELATED APPLICATIONS

This application is the U.S. national phase entry under 35 U.S.C. § 371 of International Application No. PCT/US2020/059175, filed Nov. 5, 2020, entitled SURGICAL FIXATION DEVICES AND METHODS OF USE THEREOF, which in turn claims priority to and benefit of U.S. Provisional Application No. 62/939,105, filed Nov. 22, 2019, the contents of which are incorporated herein by reference in their entirety for all purposes.

FIELD

The present disclosure relates to surgical fastening devices and, more particularly, to adjustable fastening devices for acromioclavicular (AC) joint repair.

BACKGROUND

In treating certain injuries such as acromioclavicular joint disruptions, the goal is to re-approximate bones, tendons and ligaments back to their anatomical locations to facilitate the healing process. Some current fixation devices for such repair include two fasteners which are factory assembled to a suture loop having a sliding knot. One fastener is placed on the clavicle bone and the other fastener is placed on the coracoid, with the suture loop extending between the two fasteners through passages drilled through the clavicle and coracoid. The sliding knot in the suture loop allows the distance between the two fasteners to be reduced when the suture is tensioned and thus the anatomical structures are re-approximated back to their desired locations.

In many such fixation devices, one of the fasteners must be shuttled through the passages in the clavicle and the coracoid and flipped on its side to be secured against the bone. To allow shuttling of the fastener, the passages often require a diameter of at least 4.5 mm, a size which could weaken the clavicle and/or coracoid bones and lead to postoperative fractures. In addition, the fasteners must also be small enough to pass through the passages, which could weaken the fasteners and/or increase the risk of fasteners re-migrating through the bone. Thus, an adjustable fixation device that would allow for smaller passages to be drilled through the clavicle and/or coracoid bones and which also allows for the use of larger fasteners is desired.

SUMMARY

Described herein is a suspension fixation device in which a first fastener is factory assembled to an adjustable loop of suture. The second fastener has a slot configured to allow the second fastener to be assembled to the suture loop once the suture loop has been passed through a drill hole. The second fastener further comprises a suture bridge formed through a post of the fastener for housing the suture loop while the slot is configured to prohibit the suture loop from migrating back out of the suture bridge. Advantageously, since there is no need for shuttling the second fastener through the drill hole, a smaller drill hole diameter, as well as a larger fastener size, is possible.

In examples, the surgical fastening device of this disclosure includes a first fastener coupled to a first end of an adjustable suture loop. A second fastener is configured to be assembled to a second end of the suture loop. The second fastener has a body, a post extending from the body, and a slot extending an entire width of the body for receiving the second end of the suture loop within a suture bridge defined by the post. The suture loop is able to be manipulated to change a distance between the first and second fasteners.

In further examples, the first fastener includes a generally circular body having a first surface, a second surface opposite the first surface, and a post extending from a center of the second surface and perpendicular to a long axis of the body of the first fastener. In examples, the body of the first fastener defines first and second through holes extending from the first surface to the second surface, and a recessed slot extending between the first and second through holes and at least partially formed through the post of the first fastener. The first and second through holes are configured for passage of free ends of the suture loop. In examples, the post of the first fastener defines third and fourth through holes configured for passage of the suture loop extending through a width of the post. In examples, the post of the second fastener is substantially U-shaped. In examples, the slot of the second fastener is configured for receiving the second end of the suture loop such that the second end is prevented from being pulled back out through the slot. In examples, the slot of the second fastener includes opposing sidewalls which are chamfered to converge from a largest distance to a smallest distance between the sidewalls. In examples, the smallest distance between the sidewalls extends along an entire length of the slot. In other examples, the smallest distance between the sidewalls occurs at only opposing ends of the slot. In yet further examples, the smallest distance between the sidewalls occurs only in the middle of the slot.

In examples, a method for surgical repair of this disclosure includes forming axially aligned passages between a first bone and a second bone adjacent to the first bone. An adjustable suture loop is passed through the passages. A first end of the adjustable suture loop is coupled to a first fastener. A second fastener is configured to be assembled to a second end of the adjustable suture loop by passing the second end of the adjustable suture loop through a slot extending an entire width of a body of the second fastener such that the second end of the suture loop resides in a suture bridge defined by a post of the second fastener. The adjustable suture loop is then adjusted to decrease a distance between the first fastener and the second fastener.

In further examples, the surgical repair is an acromioclavicular (AC) joint repair, the first bone is a clavicle, and the second bone is a coracoid process. In examples, the method further includes adjusting a post of the first fastener to extend into the axially-aligned passage in the first bone. In examples, the method further includes adjusting the post of the second fastener to extend into the axially-aligned passage in the second bone. In examples, the method further includes tying a security knot with free ends of the adjustable suture loop such that the security knot resides in a recess defined by a body of the first fastener. In examples, the method further includes assembling the second fastener to the second end of the adjustable suture loop with an aiding device. In examples, the second end of the adjustable suture loop comprises a cradle region. In examples, the method is performed without a scope.

Further examples of a surgical fastening device of this disclosure include a first fastener coupled to a first end of an adjustable suture loop. A second fastener is configured to be assembled to a second end of the suture loop. The second fastener has a body, a hollow post extending from the body, and at least two slots extending from opposing edges of the body toward a center of the body for receiving the second end of the suture loop extending through a center of the post. The suture loop is able to be manipulated to change a distance between the first and second fasteners.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 1A-C illustrate examples of the assembled fixation device of this disclosure;

FIGS. 2A-D illustrate examples of a first fastener for use with the fixation device of this disclosure;

FIGS. 4A-F illustrate examples of a method of use of the fixation device of this disclosure.

DETAILED DESCRIPTION

Figure 3A:
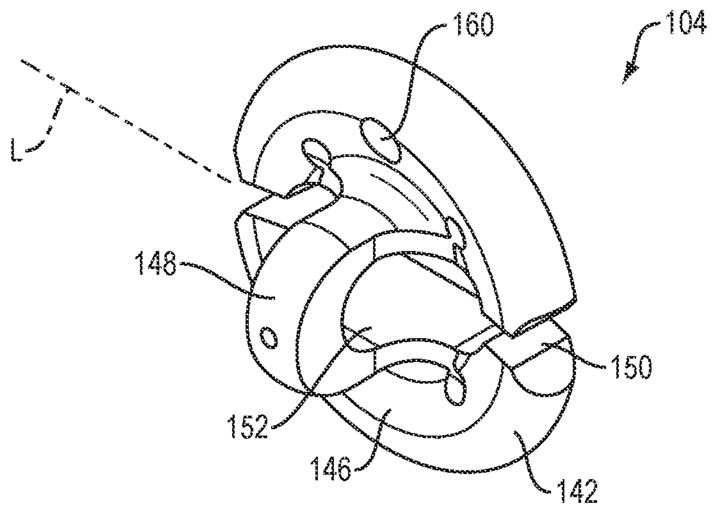
FIGS. 3A-F illustrate examples of a second fastener for use with the fixation device of this disclosure.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms “about” and “substantially” are used to represent the inherent degree of uncertainty that may be attributed to any quantitative comparison, value, measurement, or other representation. The terms “about” and “substantially” are also used herein to represent the degree by which a quantitative representation may vary from a stated reference without resulting in a change in the basic function of the subject matter at issue. “Comprise,” “include,” and/or plural forms of each are open ended and include the listed parts and can include additional parts that are not listed. “And/or” is open-ended and includes one or more of the listed parts and combinations of the listed parts. Use of the terms “above,” “below,” and the like is intended only to help in the clear description of the present disclosure and are not intended to limit the structure, positioning and/or operation of the disclosure in any manner.

Referring now to FIG. 1A, an example of a surgical fastening device 100 of this disclosure is shown in an assembled view. The device 100 can be used, for example, in the repair of an acromioclavicular joint in a patient’s shoulder. However, it is contemplated by this disclosure that the device 100 could also be scaled for use in other types of suspension fixation repair, such as a bone block procedure to repair a patient’s glenoid. In general, examples of the device 100 include a first fastener 102, a second fastener 104, at least one knotless, adjustable suture loop 106, and at least one lead suture 108. The first fastener 102 and the second fastener 104 can be made from a biocompatible metal, such as stainless steel or titanium, or plastic, such as polyetheretherketone (PEEK). The suture loop 106 and the lead suture 108 may be made of any common surgical suture material, including, for example, high-strength polyethylene.

As shown in more detail in FIGS. 1B and 1C, the first fastener 102 (FIG. 1B) is preassembled to the suture loop 106 for use in the repair. The second fastener 104 (FIG. 1C) is configured to be assembled to a cradle 107 of the suture loop 106 (that is, an area of the suture loop 106 where multiple strands of the suture loop 106 are spliced together) after the suture loop 106 has been passed through a bone hole by passing the cradle 107 through an open slot 150 of the second fastener 104, as further described below. However, it is contemplated that the second fastener 104 could also be assembled to other parts of the suture loop 106 other than the cradle 107. Free ends 138 of the suture loop 106 can be formed into a finger loop 110 that allows the distance between the first fastener 102 and the second fastener 104 to be reduced by pulling on the finger loop 110.

Turning now to FIGS. 2A and 2B, examples of the first fastener 102 include a generally circular body 112 having a first surface 114, which may be flat or slightly concave, for facing away from bone, and an opposite concave (or bowl-shaped) second surface 116, for facing bone. All edges of the body 112 may be rounded to avoid chafing of the suture loop 106 or a graft. In examples, the first fastener 102 further includes a substantially flat post 118 extending from an approximate center of the second surface 116 of the body 112 and perpendicular to a long axis L of the body 112. In other examples, not shown, the post 118 may be cylindrical or have another configuration. A length of the post 118 is selected to extend into a passageway drilled through a bone, such as a clavicle bone. The post 118 advantageously shields the strands of the suture loop 106 from cutting by the surrounding bone, while furthermore helping to center the first fastener 102 in the bone hole.

Still referring to FIGS. 2A and 2B, in examples, the body 112 defines first and second through holes 120, 122 extending between the first surface 114 and the second surface 116 of the body 112, and a recessed slot 124 extending between the first and second through holes 120, 122. In examples, the recessed slot 124 is at least partially located in a portion of the post 118 adjacent to the second surface 116 to facilitate the pulling of the post 118 into the bone hole when tension is applied to the suture loop 106. The post 118 also defines one or more additional holes, such as third and fourth through holes 126, 128 as shown, extending through a width of the post 118. The through holes 120, 122, 126, 128 are each configured for passage of at least one strand of the suture loop 106. For example, strands of the suture loop 106 may pass through holes 126 and 128 of the post 118 while the free ends 138 of the suture loop 106 may pass through holes 120 and 122 from the second surface 116 to the first surface 114 of the body 112. A fifth hole 130 may further be defined through the body 112 for passage of the at least one lead suture 108. As shown in FIGS. 2C and 2D, when the first fastener 102 is secured to a bone (for example, a clavicle 204), the recessed slot 124 is configured for receipt of a security knot 134 tied with the free ends 138 of the suture loop 106 for further increasing the strength of the fixation. The configuration of the recessed slot 124 protects the security knot 134 from contact with overlying skin or surrounding tissues, which could result in infection.

Figure 3B:
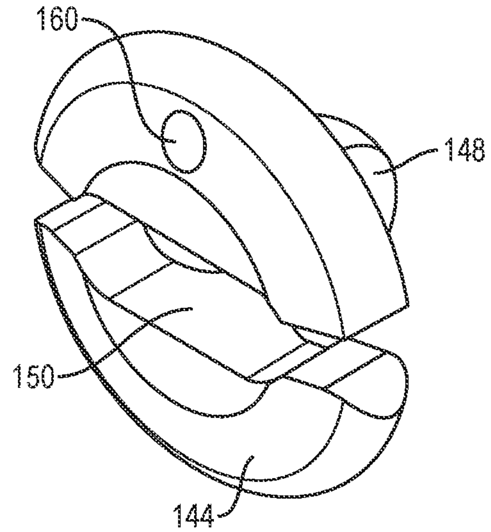

Turning now to FIGS. 3A and 3B, examples of the second fastener 104 may have the same overall length, width, and thickness as the first fastener 102. In examples, the second fastener 104 includes a generally circular body 142 having a first surface 144, which may be flat or slightly convex, for facing away from bone, and an opposite concave (or bowl-shaped) second surface 146, for facing bone. All edges of the body 142 may be rounded to avoid chafing of the suture loop 106 or a graft. The second fastener 104 further includes a post 148, which may be substantially U-shaped as shown, extending from approximately a center of the second surface 146 of the body 142 and perpendicular to a long axis L of the body 142. A length of the post 148 is selected to extend through a passageway drilled in a bone, such as a coracoid process. The body 142 defines an open slot 150 extending an entire width of the body 142 and in communication with a suture bridge 152 defined by the post 148. As further described below, the open slot 150 is configured for receipt of the cradle 107 of the suture loop 106 therethrough such that the cradle 107 may reside in the suture bridge 152 but is prevented from being pulled back out through the open slot 150. The post 148 advantageously shields the cradle 107 from cutting by the surrounding bone, while furthermore helping to center the second fastener 104 in the bone hole. A sixth hole 160 may further be defined through the body 142 for passage of the at least one lead suture 108.

Figure 3C:
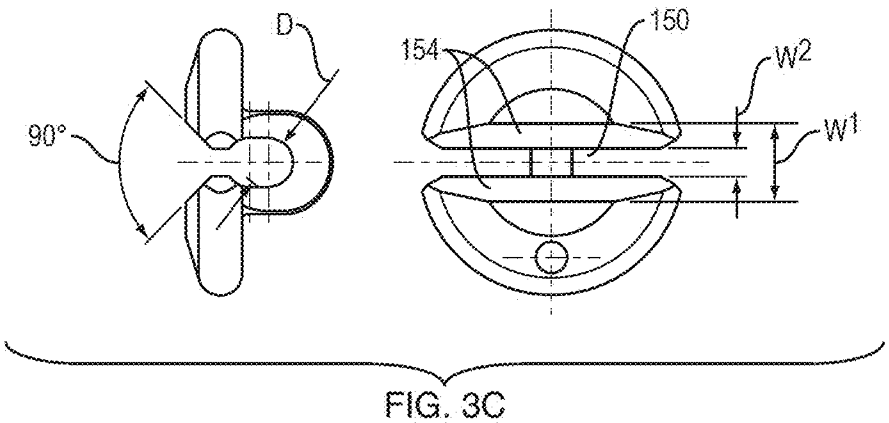
Figure 3D:
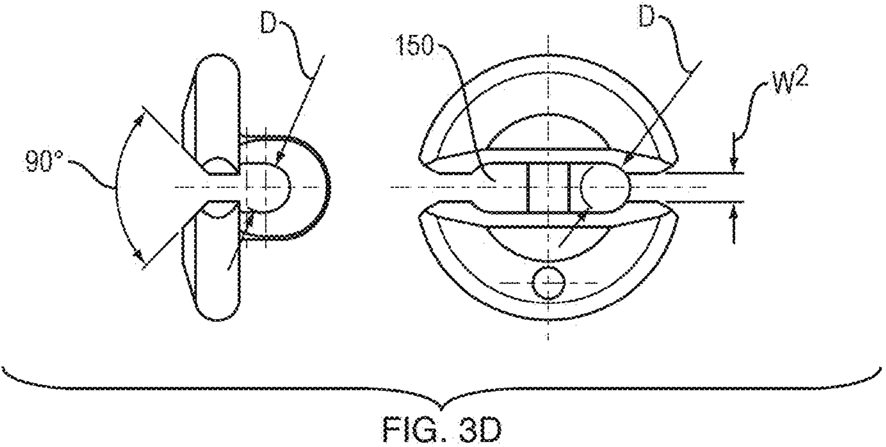
Figure 3E:
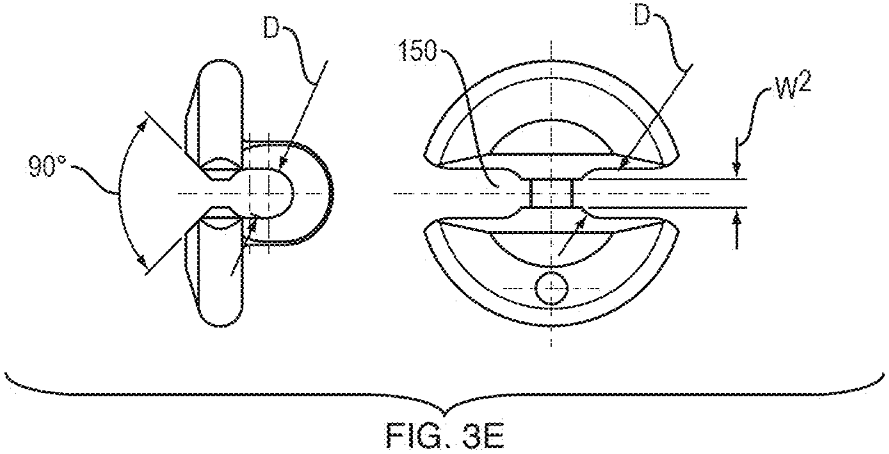
Figure 3F:
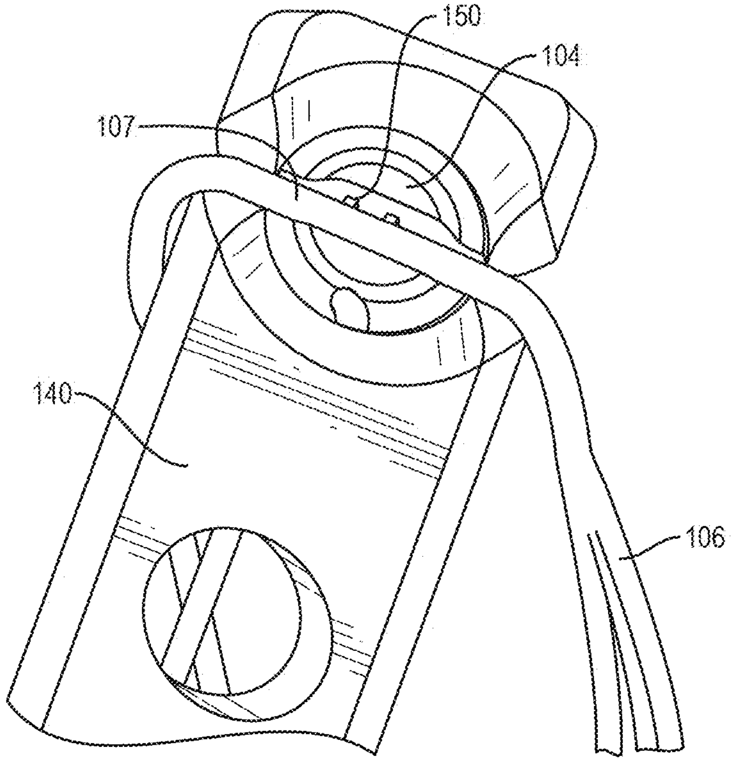

Turning now to FIG. 3C, in examples, opposing sidewalls 154 of the open slot 150 may be chamfered such that the sidewalls 154 converge from a largest width $W^1$ to a smallest width $W^2$ between the sidewalls 154 to aid in sliding the cradle 107 of the suture loop 106 through the open slot 150. In examples, an angle of the chamfer is about 90°. In examples, a smallest width $W^2$ of the open slot 150 may be about 0.9 mm, while a diameter D of the suture bridge 152 may be about 1.6 mm. In the example of FIG. 3C, the smallest width $W^2$ of the open slot 150 is the same along an entire length of the open slot 150. In other examples, the smallest width $W^2$ of the open slot 150 could occur at the outer ends of the open slot 150 (FIG. 3D), or in the middle of the open slot 150 (FIG. 3E). As shown in FIG. 3F, to facilitate the assembly procedure for the surgeon, an aiding instrument 140 could be used to hold the second fastener 104 in place while the cradle 107 of the suture loop 106 is pulled through the open slot 150. Alternatively, an area next to the cradle 107 could be pulled through the open slot 150 and the suture loop 106 could be pulled until the cradle 107 moves into the suture bridge 152.

Figure 4C:
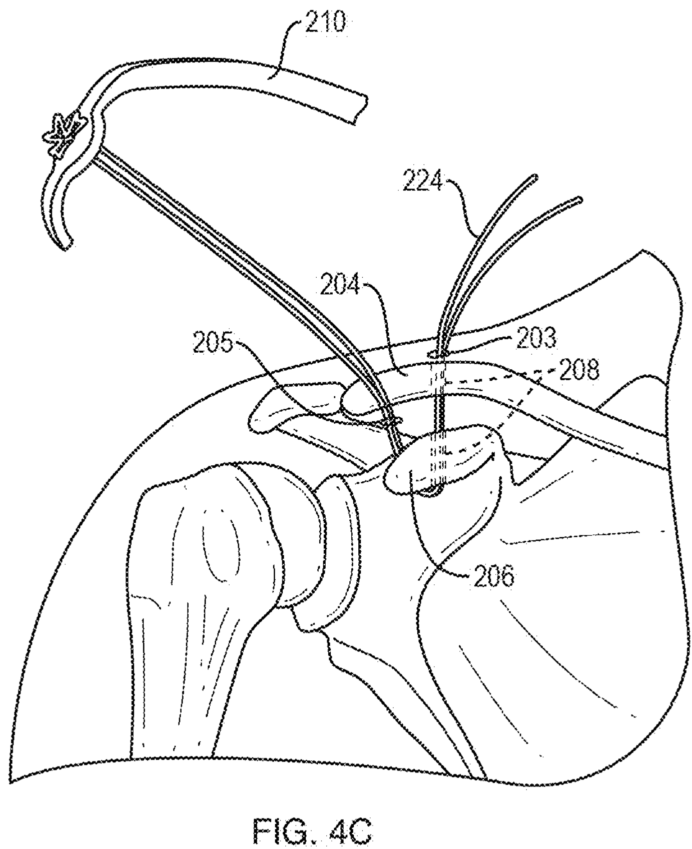

Referring to now to FIGS. 4A-F, examples of a method of using the device 100 of this disclosure in an acromioclavicular (AC) joint repair are illustrated. As shown in FIG. 4A, in which the AC joint 202 of the patient 200 is illustrated, a first skin incision 203 can be made over the clavicle 204, and a second incision 205 made between the clavicle 204 and the coracoid process 206. Additional incisions 207 can also be made, for example, for the insertion of a scope. However, in examples, the repair procedure could also be performed without a scope. As shown in FIG. 4B, a drill guide 210 is introduced into the AC joint 202 and axially-aligned passages 208 are drilled through both of the clavicle 204 and the coracoid process 206 with a drill bit 218 (for example, a 3.5 mm drill bit). A diameter of the passages 208 is selected to be less than a width of the respective bodies 112, 142 of the first and second fasteners 102, 104 such that the bodies 112, 142 cannot be pulled into the passages 208. At this point, the shoulder of the patient 200 is prepared for insertion of the surgical fastening device 100.

Figure 4D:
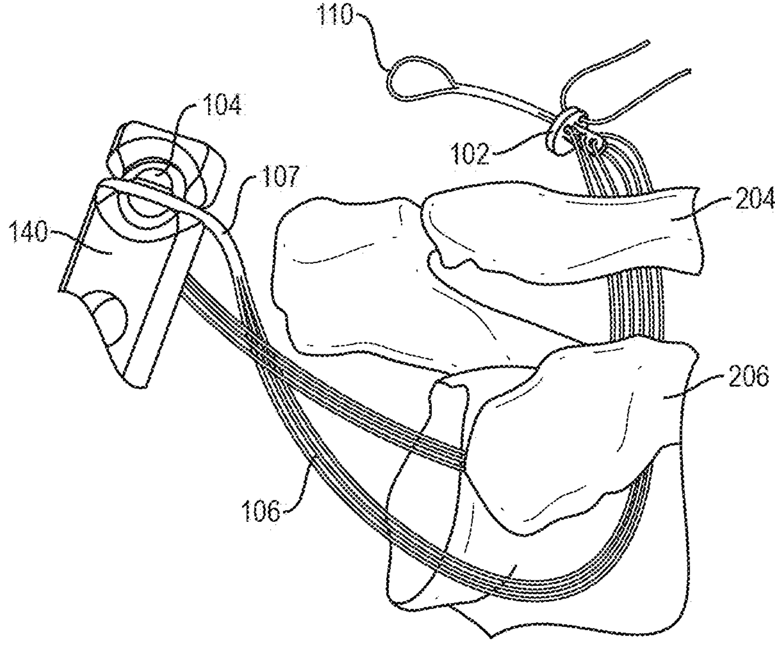
Figure 5A:
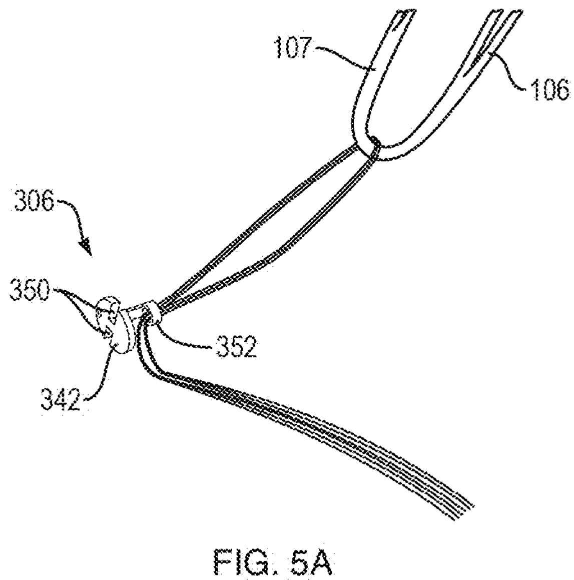
FIGS. 5A-D illustrate an alternative example of the second faster of FIGS. 3A-E.
Figure 5B:
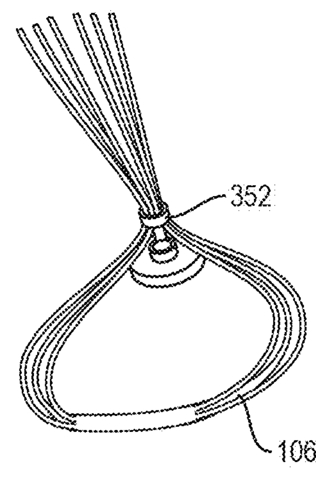
Figure 5C:
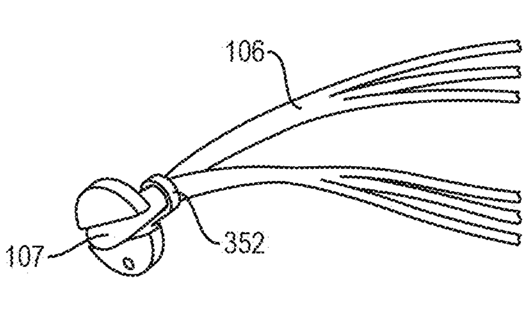
Figure 5D:
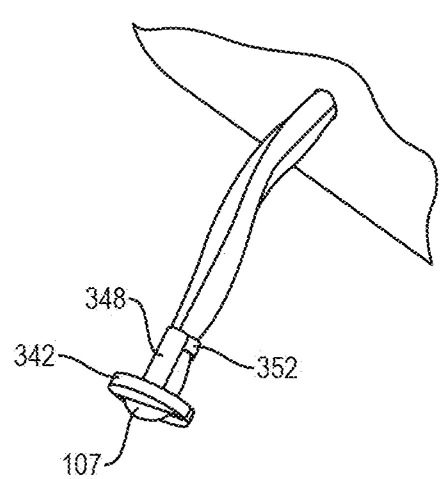

Turning now to FIG. 4C, an end of the drill guide 210 can be used to pull a shuttle suture 224 through the incisions 203, 205 and through the axially aligned passages 208 in the patient's clavicle 204 and coracoid process 206. The shuttle suture 224 can be coupled to the cradle 107 of the suture loop 106 (not shown) to pull the cradle 107 through the passages 208 such that the first fastener 102 and the finger loop 110 are positioned above the clavicle 204 and the cradle 107 is located below the coracoid process 206 (FIG. 4D). Using the aiding instrument 140, the second fastener 104 can be clipped onto the cradle 107 in the manner described above. As shown in FIG. 4E, by pulling on the finger loop 110, the suture loop 106 can be pre-tensioned, allowing the cradle 107 to pull the post 148 of the second fastener 104 into the passage 208 in the coracoid process 206 such that the second surface [136] 146 abuts the surface of the coracoid process 206. With the second fastener 104 secured to the coracoid process 206, the post 118 of the first fastener 102 can then be brought into the passage 208 of the clavicle 204 (FIG. 4F) by pulling on the finger loop 110 while retaining tension on the lead suture (not shown). With both fasteners 102, 104 in place, the device 100 can be finally tensioned, using either the finger loop 110 or a tensioning device (not shown), to manually reduce the AC joint 202. If desired, one or more security knots 134 can optionally be tied behind the first fastener 102. However, the primary fixation strength of the device 100 is carried by the cradle 107. The ends 138 of the suture loop 106 can then be trimmed. The shuttling suture 224 is then removed from the patient 200 and the incisions 203, 205 can then be closed.

Alternative examples of the second faster 306 are shown in FIGS. 5A-D. In the examples of FIGS. 5A-D, the cradle 107 of the suture loop 106 is shuttled through a partially open sleeve 352 of the post 348 and then pulled into two opposing slots 350 in the sides of the body 342 of the second fastener 306. The sleeve 352 provides a safe connection to the suture loop 106 or to the cradle 107. The geometry of the second fastener 306 confers the same benefits of shielding the suture loop 106 from bone and helping to center the post 348 of the second fastener 306 into the drill hole.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

The invention claimed is:

1. A surgical fastening device, comprising:

a first fastener coupled to a first end of an adjustable suture loop, the first fastener comprising a generally circular body having a first surface, a second surface opposite the first surface, and a first post extending from a center of the second surface and perpendicular to a long axis of the body of the first fastener; and a second fastener configured to be assembled to a second end of the suture loop, the second fastener comprising:

a body having a first surface and an opposite second surface, the body defined by a circumferential edge;

a second post extending from the second surface of the body; and a slot extending an entire length of the body between opposing points at the circumferential edge, the slot configured for receiving the second end of the suture loop within a suture bridge defined by the second post;

wherein the suture loop is able to be manipulated to change a distance between the first and second fasteners;

wherein the body of the first fastener defines first and second through holes extending from the first surface to the second surface on opposing sides of an outer surface of the first post, the first surface of the body of the first fastener further defining a recessed slot extending between and in communication with the first and second through holes and at least partially formed through the first post; and wherein the slot of the second fastener comprises opposing sidewalls that are chamfered such that the opposing sidewalls converge from a largest distance between the opposing sidewalls at the first surface of the body to a smallest distance between the opposing sidewalls at the second surface of the body, the smallest distance between the opposing sidewalls being the same along an entire length of the slot.

2. The surgical fastening device of claim 1, wherein the first and second through holes are configured for passage of free ends of the suture loop.

3. The surgical fastening device of claim 1, wherein the first post defines third and fourth through holes configured for passage of the suture loop extending through a width of the first post.

4. The surgical fastening device of claim 1, wherein the second post is substantially U-shaped.

5. The surgical fastening device of claim 1, wherein the slot of the second fastener is configured for receiving the second end of the suture loop such that the second end is prevented from being pulled back out through the slot.

6. A method for surgical repair comprising:

forming axially aligned passages between a first bone and a second bone adjacent to the first bone;

passing an adjustable suture loop through the passages, a first end of the adjustable suture loop coupled to a first fastener, the first fastener comprising a generally circular body having a first surface, a second surface opposite the first surface, and a first post extending from a center of the second surface and perpendicular to a long axis of the body of the first fastener, the body of the first fastener defining first and second through holes extending from the first surface to the second surface on opposing sides of an outer surface of the first post, the first surface of the body of the first fastener further defining a recessed slot extending between and in communication with the first and second through holes and at least partially formed through the first post;

assembling a second fastener to a second end of the adjustable suture loop by passing the second end of the adjustable suture loop through a slot extending an entire length of a body of the second fastener between opposing points at a circumferential edge of the body such that the second end of the suture loop resides in a suture bridge defined by a second post of the second fastener; and adjusting the adjustable suture loop to decrease a distance between the first fastener and the second fastener;

wherein the slot comprises opposing sidewalls that are chamfered such that the opposing sidewalls converge from a largest distance between the opposing sidewalls at a first surface of the body to a smallest distance between the opposing sidewalls at a second surface of the body, the second post extending from the second surface of the body, the smallest distance between the opposing sidewalls being the same along an entire length of the slot.

7. The method of claim 6, wherein the surgical repair is an acromioclavicular (AC) joint repair, the first bone is a clavicle, and the second bone is a coracoid process.

8. The method of claim 6, further comprising adjusting the first post to extend into the axially-aligned passage in the first bone.

9. The method of claim 6, further comprising adjusting the second post to extend into the axially-aligned passage in the second bone.

10. The method of claim 6, further comprising tying a security knot with free ends of the adjustable suture loop such that the security knot resides in the recessed slot of the first fastener.

11. The method of claim 6, further comprising assembling the second fastener to the second end of the adjustable suture loop with an aiding device.

12. The method of claim 6, wherein the second end of the adjustable suture loop comprises a cradle region.

13. The method of claim 6, wherein the method is performed without a scope.

14. A surgical fastening device, comprising:

a first fastener coupled to a first end of an adjustable suture loop;

a second fastener configured to be assembled to a second end of the suture loop, the second fastener comprising:

a body defined by a circumferential edge;

a hollow post extending from the body, the hollow post defining an interior channel extending along a longitudinal axis between a first end coupled to the body and a second open end remote from the body, a sidewall of the hollow post further having a longitudinal opening in communication with the interior channel; and at least two slots extending laterally along a same axis from a center of the body to the circumferential edge, the at least two slots configured for receiving the second end of the suture loop extending through the second open end of the post and through the interior channel of the post along the longitudinal axis and through the longitudinal opening in the sidewall of the hollow post;

wherein the suture loop is able to be manipulated to change a distance between the first and second fasteners.

* * * * *